United States Patent [19]

Engelhardt et al.

[11] Patent Number: 5,601,738
[45] Date of Patent: Feb. 11, 1997

[54] METHOD AND APPARATUS FOR TREATING MATERIAL WITH A LASER

[75] Inventors: Ralf Engelhardt, Uetze; Alfred Vogel, Lübeck, both of Germany

[73] Assignee: Medizinisches Laserzentrum Lubeck GmbH, Lubeck, Germany

[21] Appl. No.: 276,045

[22] Filed: Jul. 14, 1994

[30] Foreign Application Priority Data

Jul. 15, 1993 [DE] Germany .......................... 43 23 757.6

[51] Int. Cl.⁶ ............................ B23K 26/12; B23K 26/14
[52] U.S. Cl. ................... 219/121.84; 219/121.85; 219/121.86
[58] Field of Search .................. 219/121.84, 121.76, 219/121.77, 121.85, 121.61, 121.86, 121.69, 121.62, 121.67, 121.72; 372/6, 69; 606/11, 12

[56] References Cited

U.S. PATENT DOCUMENTS

| | | | |
|---|---|---|---|
| 4,799,755 | 1/1989 | Jones | 219/121.6 |
| 4,906,812 | 3/1990 | Nied et al. | 219/121.84 |
| 4,939,336 | 7/1990 | Meyer et al. | 219/121.62 |
| 5,246,436 | 9/1993 | Rowe | 606/13 |
| 5,254,112 | 10/1993 | Sinofsky et al. | 606/12 |
| 5,321,715 | 6/1994 | Trost | 372/6 |

FOREIGN PATENT DOCUMENTS

| | | | |
|---|---|---|---|
| 416988 | 3/1991 | European Pat. Off. . | |
| 2536573 | 2/1977 | Germany | 219/121.85 |
| 2647618 | 4/1978 | Germany | 219/121.77 |
| 231522 | 1/1986 | Germany | 219/121.85 |
| 4025566 | 2/1992 | Germany . | |
| 4105060 | 8/1992 | Germany . | |
| 56-144890 | 11/1981 | Japan | 219/121.84 |
| 61-206587 | 9/1986 | Japan | 219/121.85 |
| 62-179882 | 8/1987 | Japan | 219/121.85 |
| 2-165888 | 6/1990 | Japan . | |
| 94-24950 | 11/1994 | WIPO . | |

*Primary Examiner*—Geoffrey S. Evans
*Attorney, Agent, or Firm*—Dvorak and Traub

[57] ABSTRACT

A method and apparatus for reducing unwanted pressure changes generated during treatment of a target material in a liquid-filled space with a laser. A pilot pulse is generated to produce a gas bubble in a region of the liquid-filled space before a processing pulse is directed through the region and onto the target material. An impulse spacing between the pilot pulse and the processing pulse is optimized by detecting an oscillation period of the gas bubble. The pilot pulse and processing pulse may be generated by the same or separate laser sources and directed toward the target material by the same or separate conductors, respectively.

4 Claims, 3 Drawing Sheets

METHOD AND APPARATUS FOR TREATING MATERIAL WITH A LASER

BACKGROUND OF THE INVENTION

The invention relates to a process for material treatment by means of laser in a liquid-filled space, in which a material removal occurs by pulsewise laser emission, as well as to an apparatus for the execution of this process.

To the state of the art there belongs the practice, by means of a laser to remove material at an intended place of application by pulsewise laser emission. A special use of such a material treatment by means of laser is material removal under exclusion of of liquid. This application makes possible a finely sensitive and precise material removal such as is not feasible in this manner with other which, for example chipping processes or spark-erosive processes—which presumes the electric conductivity of the material to be removed. Thus with the known material treatment process by means of laser vessels or line systems can be treated, for example in the event of cloggings or deposits, without it being necessary to remove the liquid ordinarily present in them.

Also with this material processing, however, problems arise. Thus, for example, by ablation or by disruption in the environment of the place of application very high pressures can arise. These pressures arise through thermal expansion of the material to be removed and/or of the surrounding fluid when material is converted from the solid or liquid state into the gaseous state. In consequence of these very high pressures occurring briefly and locally, a pressure wave is radiated into the surrounding fluid and a cavitation bubble is generated, through the dynamics of which there can in individual cases occur damages to the surrounding material.

Because of the mass inertia of the surrounding liquid, a conduction system that is open per se can act in this case as a closed system. If a cavitation bubble is generated by rapid evaporation, then the mass inertia of the surrounding liquid must be overcome. Thereby there arise high pressures in the bubble interior, which lead to an acceleration outward of the bubble walls. When the interior pressure of the bubble has fallen to environmental pressure, the kinetic energy of the outward-flowing liquid is maximum. Because of the inertia forces the bubble sweeps beyond the equilibrium point. Pressure and density in the interior of the bubble fall to very low values before the bubble collapses under the outside pressure. Damages in the bubble environment can arise through the excessively high pressure at the beginning of the bubble expansion, through the kinetic energy of the outward flowing liquid and through the collapse of the bubble.

Through the local pressure increase and the bubble dynamics caused thereby there can occur an overstraining of the components or line walls lying in this region. Further, through the aforementioned pressure increases there is present the danger that in the surrounding liquid gas will be dissolved which in the subsequent pressure drop will be liberated again uncontrolled.

Underlying the invention is the problem of further developing a process according to the category in such a way that these partial strong pressure rises are reduced and also the cavitation phenomena and the aforementioned harmful effects are avoided, at least, however, clearly reduced. Further, there are to be readied suitable devices for the execution of the process of the invention.

The process part of the above problem is solved according to the invention by the means that immediately before the laser treatment gas is fed in or generated to displace the liquid present there. Underlying the present invention is the thought that the reduction of the pressure increase can occur effectively by the means that the liquid in the immediate environment of the place of application is expelled by gas, which is either supplied to this place from outside or else is generated in a suitable manner in this place immediately before the laser treatment. And, namely, the reduction of the pressure increase is all the greater the more liquid is removed before the application from the volume to be regarded in this case as closed-off. The pressure increase resulting from the generation of the gas or the supplying of the gas and the corresponding flow velocities can be kept relatively low with suitable execution.

While in the process according to the state of the art described in the preface it is not always an inconsiderable part of the liquid present around the application place which is evaporated, since the evaporation temperature of the surrounding liquid is as a rule substantially lower than that of the material to be removed, the otherwise usual strong pressure increase is responsible for not inconsiderable parts of this evaporation of the liquid, which with the process of the invention can be substantially avoided or at least strongly reduced. With the process of the invention neither is energy absorbed in the laser irradiation of the application place nor is energy lost by heat conduction from the place of application into the surrounding liquid. Furthermore, through the acoustic impedance leap on the surface of the target material it is made possible for spallation effects to arise in the target material. The bubble generation before the target material makes possible, therefore, besides the pressure reduction, also an an improvement in the ablation efficiency.

SUMMARY OF THE INVENTION

The process of the invention can be realized by two measures. For one, by a quasi static process, in which the liquid is expelled at the application place by slow supplying of gas over a line, only low flow speeds being required and, therefore, only slight pressures. After this expulsion the volume can be closed by a suitable device in order to avoid a reflux of the liquid. In the second place, the invention provides for a dynamic process in which in a fixed time ratio to the processed laser pulse gas bubbles are generated in a suitable place, preferably in the direct environment of the place of application. These gas bubbles can be generated by rapid supplying of gas or by pinpointed evaporation. For this process the dynamics of the bubble expansion or the dynamics of the supplied gas must be taken into account, since in the event of nonheeding, through the bubble dynamics there can occur a damage to the surrounding material.

If the gas at the place of application or near the place of application is to be generated by evaporation, for example by a pilot pulse preceeding the processing pulse proper, then the pilot pulse as a rule will have a substantially lower energy than the subsequent processing pulse, the pulses differ for example in their energy by a power of ten. The energy of the pilot pulse is preferably chosen in such a way that the effects arising through the pilot pulse remain underneath the threshold for damages in the environment of the place of application.

With dynamic supplying, especially generating of the gas bubble or gas bubbles in the vicinity of the place of application, the process can be optimized by the means that the time point between gas bubble build-up and the processing impulse is established so that the processing pulse removes material in the space of time in which the gas bubble generated by the pilot pulse or otherwise is in the overswing state, i.e. when the internal pressure in the gas bubble is less than the ambient pressure. Then, namely, the bubble is filled by the ablation products without a high excess pressure being generated, which would cause a renewed or continued bubble expansion. In the ideal case the pressure values caused by pilot pulse and processing pulse altogether and the generated kinetic energy of the liquid flow can be reduced to the values which result in the case of generating the bubble by the pilot pulse.

If, as provided according to the invention, not only the processing pulse, but also the bubble or bubbles are generated by laser pulse, then this can occur theoretically with one or else also with two separate lasers. Processing pulse and pilot pulse differ, however, not only in the energy feed, but they can also differ in the time duration. For the ablation one often strives for as short as possible an impulse duration, since then nearly the entire energy is absorbed in the target material and energy losses caused by heating of surrounding fluid through heat conduction is slight. With a short pulse duration, therefore, high removal rates are achieved. The pilot pulse, in contrast, which generates the gas bubble or gas bubbles will advantageously have a long impulse duration, so that the gas bubbles can be built up as slowly as possible and without abrupt pressure increase.

For the apparatus solution of the problem given further above, the invention provides various solutions. Thus, in simplest form for the generation of one or more gas bubbles, in the region of the application place parallel to the light-conductor of the laser there can be conducted a line for the gas feed, which ends in the region of the free light-conductor end and is connected in a suitable manner with a gas source. The gas to be supplied can come, for example, from a supply container, in particular a pressure container, which is connected over a valve actuatable by the control with the gas line.

If, however, a gas generation is to occur at or near the application place by a pilot pulse, then there are yielded several possibilities for the construction. If the processing laser permits, there suffices in simplest form an adaptation of the control to the effect that the pilot pulse is generated by power reduction (Leistungsreduzierung) and corresponding alteration of the impulse duration with the same laser which also generates the later processing pulse. This will not always be possible, especially not with apparatus units on hand. Then a second pilot laser with a second light-conductor can be provided, which is guided expediently together with the light-conductor of the processing laser. Further, both lasers are to be linked with one another over a corresponding control. Finally, it can be provided (which comes into consideration especially in the case of new constructions) that, to be sure, a pilot laser and a processing laser are provided, to feed these, however into the same light conductor and these are likewise linked with one another over a control in common.

Regardless of the device used, it is expedient in any case to provide a sensor which is capable, before delivery of the processing pulse, of determining dependably whether a sufficient amount of gas is present in the region of the application area, and to permit the delivery of the processing impulse only then, or, otherwise and through the control, to block the delivery of further processing pulses.

Several methods for material analysis are known, to be sure, but in the present case it will be especially simple and favorable to use an optical sensor 15. Thus, for example, processes are known in which a material determination occurs on the basis of the intensity of the reflected light. Such a material determination has the advantage that it can occur through the light-conductor of the processing laser or, if need be, also of the pilot laser, whereby the expenditure in apparatus is reduced.

In the dynamic process, the processing pulse should be triggered when the bubble generated by the pilot pulse has risen. In order to assure this a test pulse, for example, can be released with the energy of the pilot pulse and the oscillation period of the bubble thus generated is determined. The oscillation period is yielded from the time difference between the pressure waves that are emitted in the bubble generation and in its collapse and can, therefore, be determined acoustically through an acoustic pressure sensor 17 in a simple manner.

BRIEF DESCRIPTION OF THE DRAWING

The apparatus development of the invention is explained in the following with the aid of three examples of execution represented in highly schematic form in the drawings.

DETAILED DESCRIPTION OF THE INVENTION

Figure 1:
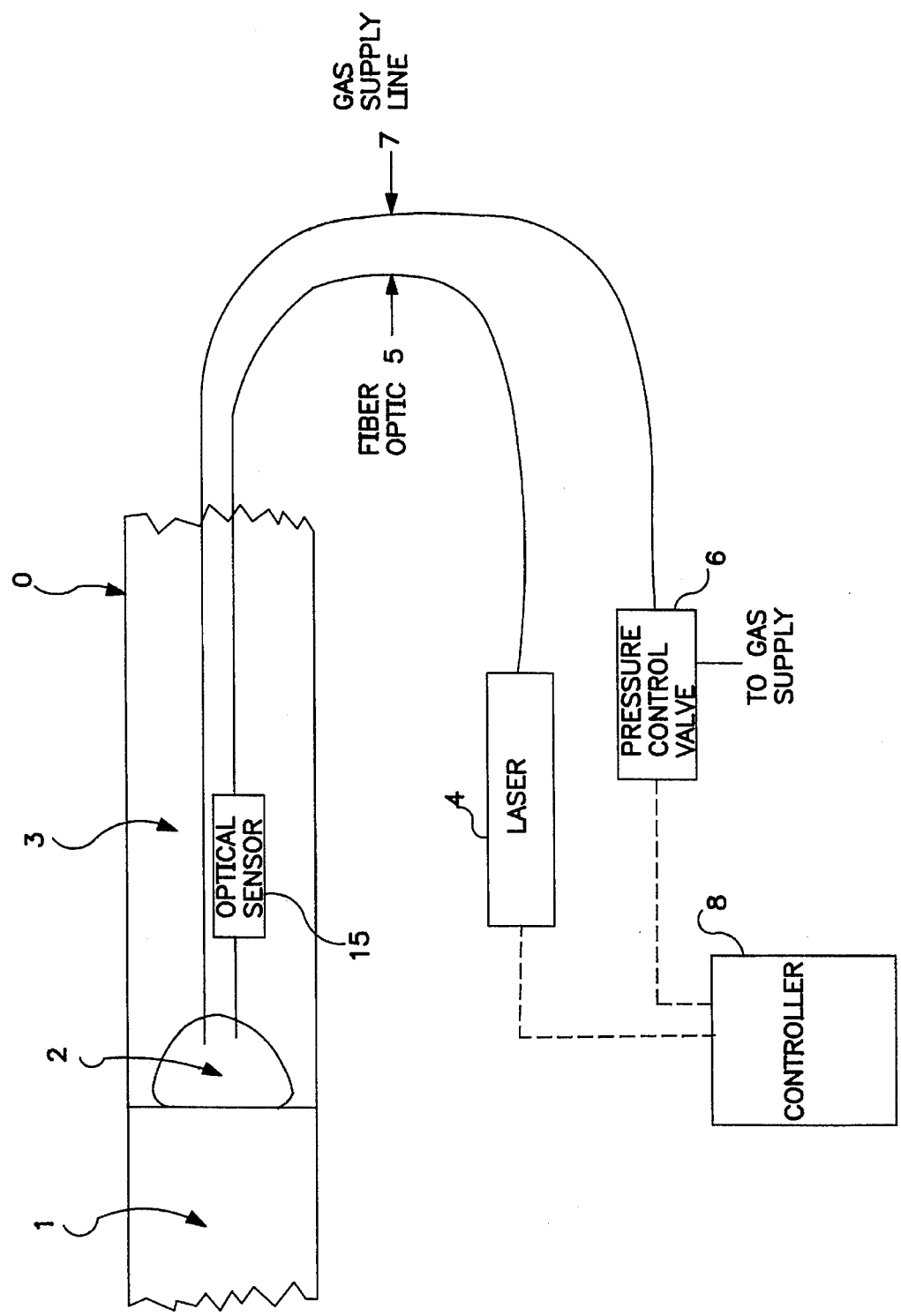
FIGS. 1 to 3 show in each case the schematic construction of these devices.

In the figures a part of a pipline 0 is represented which is stopped by a plug 1. The liquid present in the pipeline is designated with 3. The process of the invention is to be used in order, by laser treatment, to remove the plug 1 in the pipeline 0 and in this manner to make the pipeline passable again. During the treatment there is liquid 3 present in the line. The gas bubble to be provided according to the invention for the material-removing treatment is designated with 2 and is located immediately in front of the material 1 to be removed.

In the execution according to FIG. 1 the device has a laser 4 which forms the processing laser and to which a light-conductor 5 is connected, the free end of which ends in the pipeline 0 shortly before the plug 1, therefore near the application place. The gas bubble 2 is formed by the gas conveyed through the line 7, which comes from a supply container which is connected, over a valve actuated by a control 8, with the line 7. The control 8, which is provided for the drive of the laser 4, provides that on input of a corresponding control signal gas is conducted first over the arrangement 6 and the line 7 to the application place, so that the gas bubble 2 forms. As soon as bubble 2 is detected by optical sensor 15 or else after a predetermined time span the control 8 then triggers an impulse of the laser 4, which is directed over the light-conductor 5 onto the application place, i.e the plug 1. This process is repeated until the desired removal result is achieved.

Figure 2:
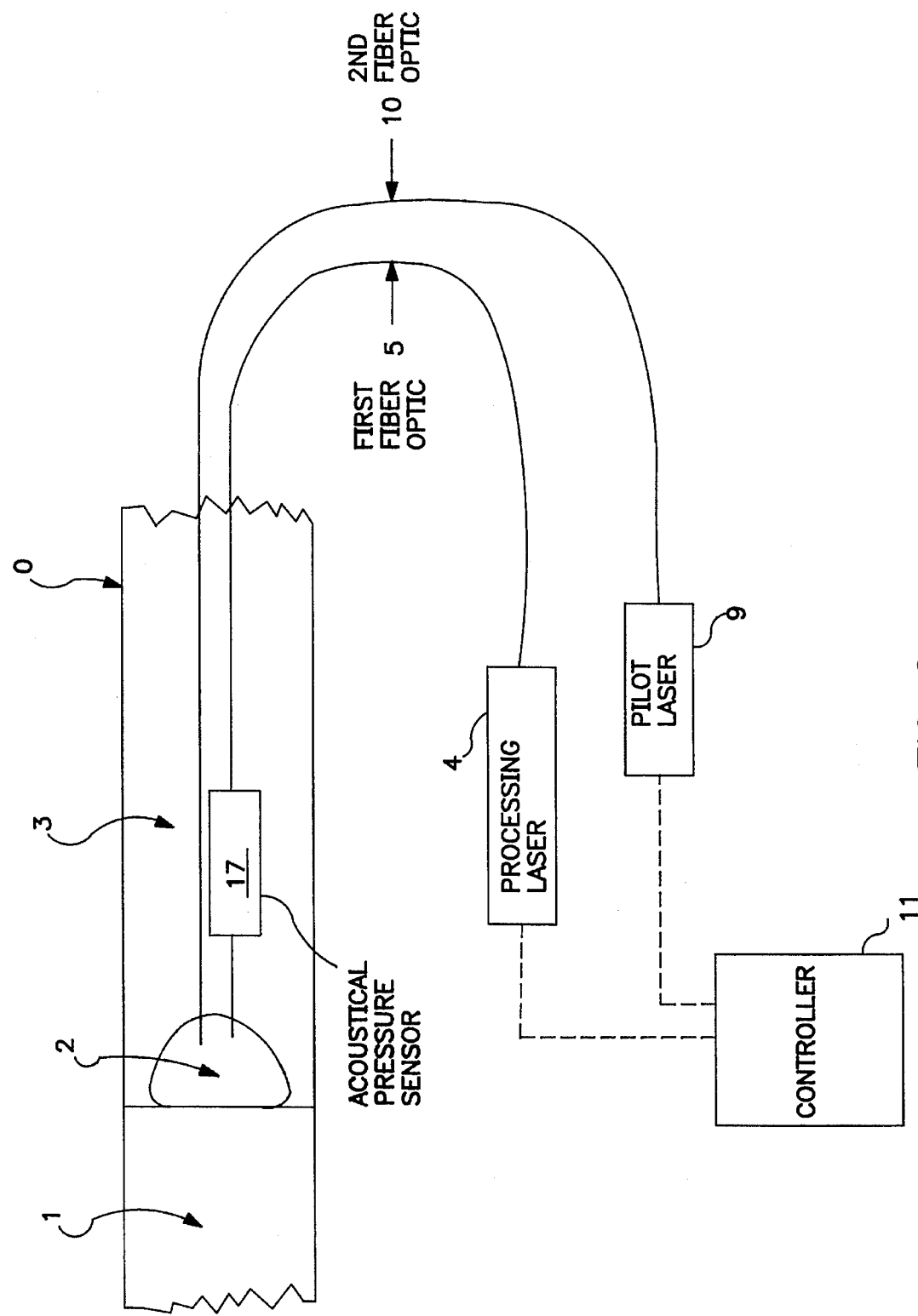

The execution according to FIG. 2 differs from the one previously described in that, instead of the arrangement 6 for the gas conduction by means of line 7 a second laser 9, a so-called pilot laser, is provided, which is led over a second light-conductor 10 together with the light-conductor 5 up to the application place. Both the processing laser 4 and also the pilot laser 9 are driven over a control 11 in such manner that by means of the pilot laser 9 there is first sent a comparatively long and energy-poor laser pulse to the application place for the purpose of forming the gas bubble 2, and that only after formation and collapse of the gas bubble 2 is acoustically measured by sensor 17 is there released the comparatively energy-rich and brief pulse of the processing laser 4. Instead of the two light-conductors 5 and 10 represented, there can also be used a common light-conductor, in which there is input over corresponding optical means from both lasers 4 and 9.

Figure 3:
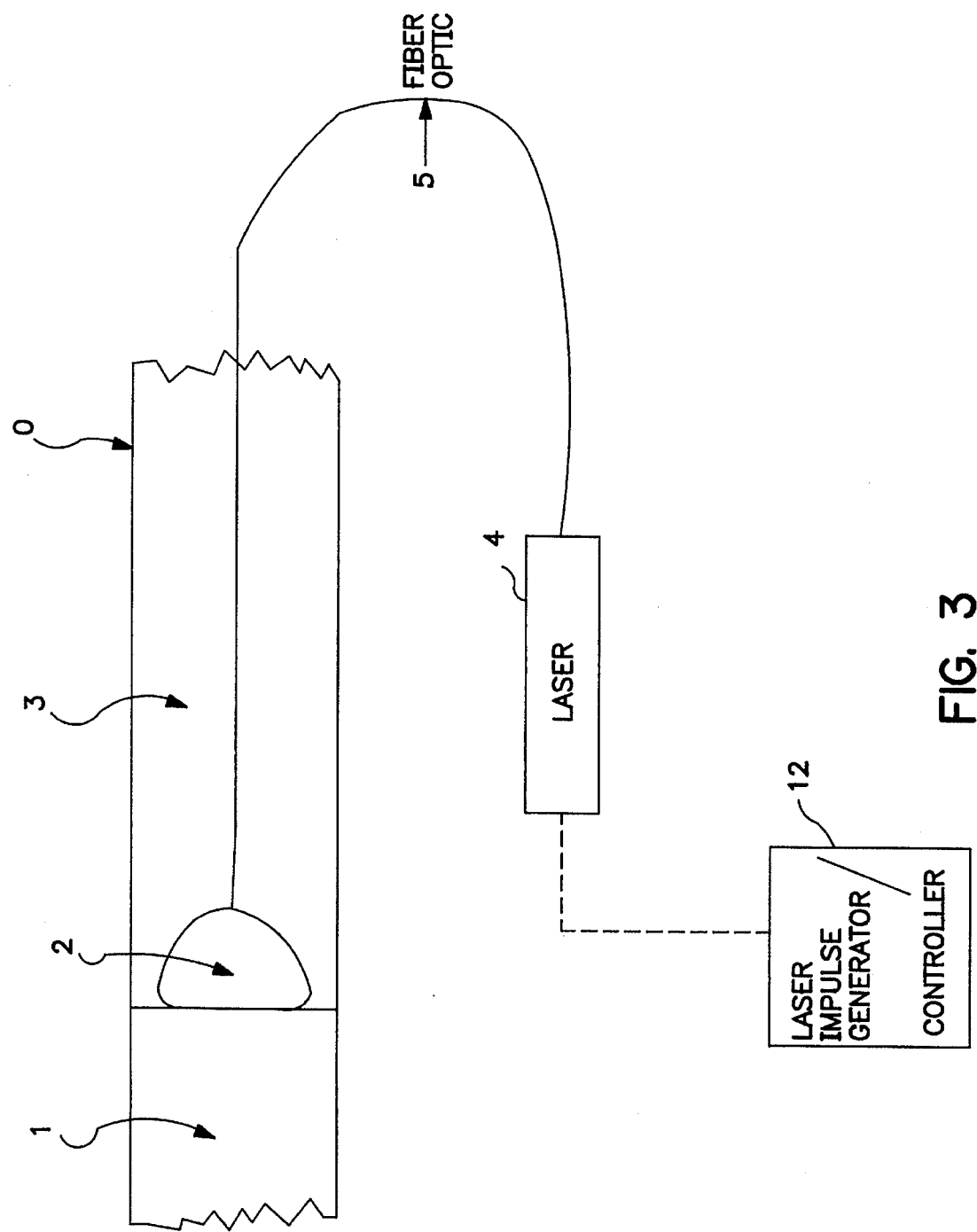

In the execution according to FIG. 3 only one laser 4 is provided, the output of which is conducted over the light-conductor 5 to the application place. In this execution a control 12 takes over not only the freeing of the processing pulse of the laser 4, but further controls the performance of the laser 4, the impulse duration and the impulse spacing. In this manner, the laser 4 can be driven both for the delivery of a pilot pulse and also for the delivery of a processing pulse.

The foregoing is a description enabling one of ordinary skill in the art to make and use the preferred embodiments of the present invention. It will be appreciated by those skilled in the art that there exist variations, modifications and equivalents to the embodiments disclosed herein. The present invention therefore is to be limited only by the scope of the appended claims.

We claim:

1. A process for reducing unwanted pressure changes generated during treatment of a target material in a liquid-filled space with a processing pulse from a processing pulse laser source, wherein the processing pulse laser source and the target material are separated by the liquid, the process comprising steps of:

generating the processing pulse and directing the processing pulse onto the target material to be treated;

generating a pilot pulse with a pilot pulse laser source that has sufficient power to produce a sufficiently large gas bubble by evaporation in a region of the liquid-filled space between the processing pulse laser source and the target material to be treated, wherein the pilot pulse laser precedes the processing pulse so that the processing pulse is directed through the gas bubble and onto the target material in order to reduce unwanted pressure changes sufficient to damage material other than the target material; and then optimizing an impulse duration spacing between the pilot pulse and the processing pulse by detecting an oscillation period of the gas bubble produced by the pilot pulse, wherein immediately after said bubble bursts, said processing pulse is generated and directed to said target material.

2. A method of irradiating a target material with laser radiation from a laser source, said target material located within and obstructing an interior of a liquid conveyance means which has interior walls, said radiation delivered to said target material through a first fiber optic conductor having a terminal end in closely spaced proximity from said target material, said space between said terminal end and said target material occupied with a liquid within said liquid conveyancing means, said method comprising the steps of:

providing a second fiber optic conductor alongside of said first fiber optic conductor;

providing a means for removing said liquid from said space, comprising a pilot laser pulse generated from said laser source, said pilot pulse of a relatively long duration and low energy and delivered to said target material over said second fiber optic conductor, said pilot laser pulse creating a vapor bubble in said liquid material, wherein said bubble is slowly generated so not to create a pressure shockwave within said interior of said liquid conveyancing means, said bubble absorbing energy from said pilot laser pulse and eventually bursting, wherein said liquid is displaced away from said target material when said bubble bursts;

generating a processing laser pulse of a relatively short impulse duration and high energy so that said high energy pulse is delivered through the first fiber optic conductor directly to the target material for removal thereof, wherein removal of said liquid eliminates a source of relatively high and damaging pressure against said target material and said interior of said conveyancing means which is normally generated when said liquid is vaporized during exposure to said laser pulse, and wherein removal of said liquid reduces energy losses associated with said liquid normally resulting from heat absorption and conduction during said exposure to said processing laser pulse, thereby allowing a greater ablation efficiency in removing said target material, without damage to said interior walls as normally caused by said pressure source.

3. A laser system for irradiating a target material with a laser beam, said target material disposed within a liquid conveyancing means and being immersed in a liquid medium, said system comprising:

a means for generating a laser beam;

a fiber optic conductor for delivering said laser beam to said target material;

means for controlling said laser beam generation, wherein said controller means functions to cause a first and pilot laser pulse to be generated having a low energy level of a relatively long impulse duration so as to slowly form a vapor bubble in said liquid medium near said target material, said bubble slowly forming so as not to create a damaging pressure shock wave within said liquid conveyancing means, said pilot laser pulse conducted to said bubble by said controller means for a predetermined time so as to burst said bubble and displace said liquid away from said target material, wherein said controller further functions to cause a second and processing laser pulse to be generated immediately after said bubble bursts, so that said processing laser may be delivered to said target material without irradiating any of said liquid medium, thereby maximizing the laser radiation reaching said target material, said system including a means for detecting an oscillation period of the gas bubble produced by the pilot pulse in order to optimize an impulse duration time spacing between the pilot pulse and the processing pulse, wherein the pilot pulse has an energy less than an energy of the processing pulse by a factor of approximately ten.

4. The apparatus according to claim 3 wherein the processing pulse is generated only if a gas bubble is detected near said target material.

* * * * *